(12) United States Patent
Chefles et al.

(10) Patent No.: US 10,049,182 B2
(45) Date of Patent: Aug. 14, 2018

(54) HEALTH MONITORING

(75) Inventors: Anthony Chefles, Oxford (GB); Rory Morrison, Oxford (GB); Rebecca Weir, Oxford (GB); Keith Errey, Oxford (GB)

(73) Assignee: ISANSYS LIFECARE LIMITED, Abingdon, Oxfordshire (GB)

( * ) Notice: Subject to any disclaimer, the term of this patent is extended or adjusted under 35 U.S.C. 154(b) by 332 days.

(21) Appl. No.: 13/983,592

(22) PCT Filed: Feb. 3, 2012

(86) PCT No.: PCT/GB2012/050245
§ 371 (c)(1),
(2), (4) Date: Nov. 8, 2013

(87) PCT Pub. No.: WO2012/104658
PCT Pub. Date: Aug. 9, 2012

(65) Prior Publication Data
US 2014/0058280 A1 Feb. 27, 2014

(30) Foreign Application Priority Data
Feb. 3, 2011 (GB) .................................. 1101858.7

(51) Int. Cl.
A61B 5/04 (2006.01)
G06F 19/00 (2018.01)
(Continued)

(52) U.S. Cl.
CPC ........ G06F 19/3418 (2013.01); A61B 5/0006 (2013.01); A61B 5/0402 (2013.01);
(Continued)

(58) Field of Classification Search
CPC . A61B 5/0456; A61B 5/0452; A61B 5/02438; A61B 2560/0431
(Continued)

(56) References Cited

U.S. PATENT DOCUMENTS 3,943,918 A 3/1976 Lewis
5,749,367 A 5/1998 Gamlyn et al.
(Continued)

FOREIGN PATENT DOCUMENTS

CN 201701206 U 1/2011
GB 2425181 10/2006
(Continued)

OTHER PUBLICATIONS

O. Escalona, et al.; "An Algorithm for Microprocessor-Based QRS Detection", Journal of Clinical Engineering USA, vol. 11, No. 3, May 1896, pp. 213-219.
(Continued)

Primary Examiner — Eric D. Bertram
Assistant Examiner — Elizabeth K So
(74) Attorney, Agent, or Firm — Eversheds Sutherland (US) LLP

(57) ABSTRACT

Health monitoring devices allow for monitoring of the vital signs of a subject. Wireless devices can enable a subject's cardiac and/or respiratory functions to be monitored remotely, e.g. without the subject being attached to bedside equipment. A cardiac monitoring device may include a substrate, electrodes for measuring ECG signals, and an electronics module including a data processor and a wireless transmitter. The electronics module is sealed within the substrate and arranged to receive the measured ECG signals. Each ECG signal associated with a heartbeat is processed in the data processor to provide key data relating to that heartbeat. The key data may include the temporal position of a characteristic feature in the ECG signal. The key data is provided to the wireless transmitter for transmission.

10 Claims, 5 Drawing Sheets

(51) Int. Cl.
  *A61B 5/00* (2006.01)
  *A61B 5/0456* (2006.01)
  *A61B 5/0402* (2006.01)
  *A61B 5/024* (2006.01)
  *A61B 5/0245* (2006.01)

(52) U.S. Cl.
  CPC .......... *A61B 5/0456* (2013.01); *A61B 5/0245* (2013.01); *A61B 5/02405* (2013.01); *A61B 5/02438* (2013.01)

(58) Field of Classification Search
  USPC ........................................................ 600/521
  See application file for complete search history.

(56) References Cited

U.S. PATENT DOCUMENTS

| | | | |
|---|---|---|---|
| 6,491,647 B1* | 12/2002 | Bridger | A61B 5/021 128/900 |
| 6,602,201 B1* | 8/2003 | Hepp | A61B 5/02028 600/526 |
| 7,381,188 B1* | 6/2008 | Farazi | A61B 5/0452 600/508 |
| 2006/0041281 A1 | 2/2006 | Von Arx et al. | |
| 2007/0276270 A1* | 11/2007 | Tran | A61B 5/0022 600/508 |
| 2007/0293781 A1* | 12/2007 | Sims | A61B 5/1135 600/534 |
| 2010/0004517 A1 | 1/2010 | Bryenton et al. | |
| 2010/0036207 A1* | 2/2010 | Eckblad | A63B 69/32 600/300 |
| 2010/0075115 A1 | 3/2010 | Tuerk et al. | |
| 2010/0219847 A1 | 9/2010 | Douglas | |
| 2010/0312188 A1* | 12/2010 | Robertson | A61B 5/0006 604/156 |
| 2010/0331711 A1 | 12/2010 | Krauss et al. | |

FOREIGN PATENT DOCUMENTS

| | | |
|---|---|---|
| WO | 97/08989 A1 | 3/1997 |
| WO | 2008/010133 A2 | 1/2008 |
| WO | 2008/135952 A1 | 11/2008 |
| WO | 2008/142365 | 11/2008 |
| WO | 2010/075115 A2 | 7/2010 |

OTHER PUBLICATIONS

V. Bhargava, et al.: "Progress in Computer Analysis of the Exercise Electrocardiogram", American Journal of Cardiology, Cahners Publishing Co., Newton, MA, US, vol. 47, No. 5, May 1, 1981, pp. 1143-1151.

X Chen, et al.; "Reliable Automated QT Interval Measurement for Clinical Evaluation"; computers in Cardiology—2006 Computers in Cardiology, CIC 2006 Inst. of Elec. And Elec. Eng. computer Society US, vol. 33, 2006, pp. 373-376.

R.F. Yazicioglu, et al.; Ultra-Low-Power Wearable Biopotential Sensor Nodes, 31st Annual International conference of the IEEE EMBS Minneapolis Minnesota, Sep. 2-6, 2009.

Gene Ostrovsky, A Wireless ECG Patch, medGadget, Oct. 31, 2007.

IMEC, Integrated Wearable Systems (body area networks), IMEC Scientific Report 2010, Aug. 1, 2011.

J. Vanfleteren; Flexible & Stretchable Circuits, IMEC, Euripedes Forum 2010 Paris, Sep. 30-Oct. 1, 2010. pp. 5-11.

IMEC; Packaging & Integration Technology for Wearable and Implantable Applications, IMEC Scientific Report 2010, Aug. 1, 2013.

Chris Otto, et al, Title: System Architecture of a Wireless Body Area Sensor Network for Ubiquitous Health Monitoring, Journal of Mobile Multimedia, vol. 1, No. 4 (2006), pp. 307-326.

* cited by examiner

HEALTH MONITORING

TECHNICAL FIELD

The present invention relates to health monitoring devices which allow monitoring of the vital signs of a subject, particularly although not exclusively to wireless devices that allow a subject's cardiac and/or respiratory functions to be monitored remotely e.g. without the subject being attached to bedside equipment.

BACKGROUND OF THE INVENTION

In recent years there has emerged a new class of small body worn devices that monitor one or more vital signs and transmit the readings wirelessly to a receiver unit without encumbering a patient with cables. For example, wireless and self-adhesive electrocardiography (ECG) monitors, which are placed on a subject to permit the remote monitoring of cardiac rhythm, are known e.g. from U.S. Pat. No. 3,943,918. A short-range wireless connection such as Bluetooth™ may be used. Typically the wireless receiver unit retransmits the data to an IT system for processing and display. The data (raw and/or processed) may be stored in a data base or electronic medical record. Within the IT system or individual patient record various "rules" may operate to alert medical staff when one or more of the vital signs moves outside the limits set for a patient.

In the context of cardiac monitoring using electrocardiography (ECG) electrodes, especially self-adhesive electrodes, wireless transmission of the raw ECG readings is possible but to transmit the entire ECG signal requires large amounts of bandwidth and consequently the monitoring device must be able to provide sufficient transmitting power. In order to alleviate such problems it has been proposed to set up the monitoring device so that the ECG signal is only sampled at pre-programmed intervals, for example once every 2, 5 or 10 minutes. The wireless power consumption scales proportionally with sampling rate. This enables the average heart rate to be calculated without requiring near-continuous transmission of data and thereby lowers the power consumption of the wireless transmitter. However this approach does not allow every heartbeat and its associated ECG peak to be recorded and potentially processed. Such a quasi-continuous measurement of heart rate may not reveal cardiac arrhythmias or other information useful for clinicians.

On the other hand, it has been proposed to perform full data processing on a wireless ECG sensor node rather than transmitting raw data. It has been reported, however, that in previous attempts the increased power consumption from local processing counteracts the limited savings in the radio power from a reduced rate of data streaming. There remains a need for an effective system for local ECG signal processing and data transmission.

It is also known to provide wireless heart rate monitors which are held against the patient by a chest strap. Using a chest strap for support means that it can be possible to mount a larger wireless transceiver including a data processor that is able to process and/or transmit instantaneous data relating to cardiac function. However, not only do such devices tend to be heavy and bulky but the degree of contact with the skin is generally poor and prone to motion artefacts. Moreover the need for a chest strap to be fitted around the subject means that such monitors may not be suitable in trauma situations where the subject is physically injured or disabled.

Monitoring devices that combine heart rate measurement with other vital signs, such as temperature and respiration rate, generally utilise separate sensors for each parameter and read each sensor sequentially. In addition to failing to provide continuous readings, such devices are also unable to provide concurrent data, for example simultaneous heart rate and respiration rate measurements.

SUMMARY OF THE INVENTION

The Applicant has appreciated that known monitoring devices suffer from various shortcomings. It is an object of the present invention to provide improved monitoring devices for cardiac rhythm and potentially other vital signs, which aims to alleviate at least some of the shortcomings of known devices.

According to a first aspect of the present invention there is provided a cardiac monitoring device comprising a substrate, means for measuring ECG signals, data processing means comprising a data processor, and a wireless transmitter, wherein the data processing means is sealed within the substrate and arranged to receive the measured ECG signals, to process each ECG signal associated with a heartbeat in the data processor to provide key data relating to that heartbeat, and to provide the key data to the wireless transmitter for transmission.

It will be understood that devices in accordance with the invention do not necessarily discard any data from the measured ECG signals. The data processing means is arranged to receive the measured ECG signals on a near-continuous basis such that every ECG signal corresponding to a heartbeat is sampled by the data processor. Thus important information relating to a subject's cardiac rhythm is not lost. However the device is able to reduce the bandwidth, and hence the power, required to transmit information from the device by processing each ECG signal and extracting key data relating to every heartbeat which is then provided to the wireless transmitter. Rather than transmitting all of the raw ECG data, the data processor extracts a limited amount of key data, e.g. by applying one or more algorithms, which is then made available by the wireless transmitter. Furthermore, key data is only provided when a heartbeat is detected. The extraction of key data will be described in more detail below.

It is a particular advantage of the invention that the data processing means is powerful enough to be able to provide the key data while also being e.g. small enough to be sealed inside the substrate of the device. Accordingly there is provided an integrated device that may be comparable in processing power with a separate data processing/transmitting unit but which can be attached to a subject as a unitary device. The wireless transmitter may also be sealed within the substrate. The wireless transmitter may be provided separately or integrally with the data processing means. As a result of its integrated structure, the monitoring device may find use in a wide number of different medical situations, ranging from emergency monitoring in a trauma situation, to routine monitoring of a patient on a hospital ward, and to back-up monitoring of a subject in his or her own home.

The data processor has the function of processing ECG signals so as to provide key data relating to every heartbeat. Typically the most important raw data associated with an ECG signal is the R-S amplitude and/or time stamp for the QRS complex peak produced in the ECG by a heartbeat. The Applicant has recognised that processing raw ECG signals to extract the amplitude and time values associated with the R-peak for each heartbeat represents an efficient way to reduce the local power demand without compromising the data content that is transmitted. This data, in particular the R-R peak temporal spacing, can be used to calculate the heart rate (HR) using a relatively straightforward algorithm and thus in some embodiments the key data may therefore comprise a measurement of heart rate (HR).

However, in other embodiments it is preferable to minimise the calculations that are carried out by the data processor in the device and thus key data comprising the time stamp for the QRS complex peak is preferably sent by the wireless transmitter to be further processed elsewhere. Furthermore it is advantageous for the key data to include at least one piece of amplitude data in addition to the time stamp of the R-peak. In a preferred set of embodiments the amplitude data is the value of the R-S amplitude in the ECG signal, as a peak detection algorithm run in the processor may conveniently identify the R-S amplitude in order to determine the temporal position of the R-peak. Thus according to a second aspect of the present invention there is provided a cardiac monitoring device comprising: a substrate; means for measuring ECG signals; data processing means comprising a data processor; and a wireless transmitter; wherein the data processing means is sealed within the substrate and arranged to receive the measured ECG signals, to process each ECG signal associated with a heartbeat in the data processor to provide key data relating to that heartbeat, and to provide the key data to the wireless transmitter for transmission, wherein the key data is the R-S amplitude and time stamp for the QRS complex peak produced in the ECG signal by a heartbeat.

The processor may be programmed to run a peak identification algorithm that can identify the QRS complex in the ECG signal (shown in FIG. 1). In particular, a windowing algorithm can make use of the fact that the range of amplitude values in the QRS complex is, in a normal sinus rhythm, substantially greater that at any other point in the ECG signal for a cardiac cycle. Thus, by applying a time window to isolate the ECG signal associated with a given heartbeat and looking for the difference between the maximum and minimum amplitudes (i.e. the amplitude range) in that window, the amplitude difference will be substantially greater when the window contains the downward stroke from the peak of the R-wave to the bottom of the S-wave (see FIG. 1). An advantage of using amplitude changes to identify characteristic features such as the QRS complex is that the method is independent of the absolute amplitudes of the R- and S-peaks. Reliable peak detection may therefore be achieved even under conditions of significant wandering of the baseline signal. Furthermore, even if the ECG measurement (e.g. electrode) position is changed and the absolute amplitudes of the R- and S-peaks are altered, the same method can identify the QRS complex more reliably than detection techniques that rely on absolute measurement of amplitude features relative to the baseline.

A peak identification algorithm that uses the measured amplitude changes for detection can reliably eliminate the T-wave when identifying the R-peak, or vice versa. Firstly, the gradient of the amplitude change is typically much lower for a T-wave than during the R-S phase of the cardiac cycle so the amplitude range is considerably lower. Secondly, even if the T-wave were to have an absolute amplitude comparable to the R-wave, by looking for a maximum amplitude difference the algorithm can identify the QRS complex from the amplitude dip following the R-peak to a minimum at the S-wave, which enables it to be distinguished from the T-wave.

It is desirable that the key data extracted from an ECG signal comprises at least the temporal position of the R-peak and the R-S amplitude. The R-peak spacing can be used to later calculate the heart rate (as mentioned above), while the R-peak or R-S amplitude is known to vary in synchrony with a patient's respiratory cycle and may therefore be used to calculate heart rate variability and/or respiration rate (as will be described below). However, for different patients and/or in different clinical settings the device may be used to monitor a range of cardiac occurrences based on time and/or amplitude values other than those associated with the R-peak. Furthermore the position of the ECG measuring means (e.g. electrode lead position) can change the cardiac view and the relative magnitudes of the characteristic features (P-wave, QRS complex, T-wave) seen in the ECG signal. Preferably the key data comprises at least the temporal position of one of the characteristic features in the ECG signal. As will be understood from FIG. 1, these characteristic features can each provide a marker in the ECG signal that the processor can then use to identify other features of interest e.g. according to their relative position and/or amplitude. Further component(s) of the key data, corresponding to one or more pre-defined features of the ECG signal, may be identified for a range of purposes. Starting from the temporal position of one of the characteristic features, various further features of the ECG signal may be identified by measuring the amplitude changes in time e.g. using methods analogous to the peak identification algorithm mentioned above.

Thus according to a third aspect of the present invention there is provided a cardiac monitoring device comprising a wearable unit comprising: means for measuring ECG signals; data processing means comprising a data processor; and a wireless transmitter; wherein the data processing means is sealed within the substrate and arranged to receive the measured ECG signals, to sample each ECG signal associated with a heartbeat, to process the sampled signal data in the data processor to extract key data relating to that heartbeat, and to provide the key data to the wireless transmitter for transmission; and wherein the processor is programmed to apply a time window to the sampled data to isolate at least a portion of the data associated with a given heartbeat and measure the amplitude changes in that window, the amplitude changes being used to identify key data comprising the temporal position of a characteristic feature in the ECG signal and at least one further time or amplitude value corresponding to one or more pre-defined features of the ECG signal.

It will be understood that the characteristic features in a human ECG signal are the peaks and troughs of the ECG waveform conventionally labelled P, Q, R, S and T, e.g. as shown in FIG. 1, and typically referred to as the P-wave, QRS complex, and T-wave. The presence and/or relative appearance of these characteristic features in the ECG signal may depend on the bodily position of the ECG measuring means, as well as varying from patient to patient and changing in time e.g. due to health conditions. For example, with ECG measuring electrodes in the Lead I position the R-peak is expected to be larger than the T-wave, but in the V3 or V4 position the T-wave may be a stronger feature than the R-peak. However, at least one of the characteristic features will always be present and thus identifying its temporal position can provide a marker enabling the processor to look for other features in the ECG signal. Preferably the processor is programmed to identify one of the "strong" characteristic features in the ECG signal as the temporal marker which then facilitates detection of other features, i.e. the characteristic feature is preferably the R-peak or T-wave.

It will be appreciated that devices according to this aspect of the invention benefit from a particularly efficient data processing regime in the onboard processor. Rather than transmitting all of the raw data sampled from the ECG signal, the processor is programmed to look for certain key data that can be attributed to features of interest, and potentially of clinical significance, in the ECG signal arising from each heartbeat. Furthermore, rather than simply applying a window to a portion of the signal of interest and transmitting all of the data in that window, the processor extracts a time or amplitude value as a piece of key data and discards other data in the heartbeat window. The processor has been programmed so that it is intelligent enough to look for one or more specific features of the ECG signal and only extract key data for transmission when the features are found. The processing therefore goes beyond mere data compression. By programming the processor to apply a data analysis tailored for identification of particular feature(s) in the ECG signal, the processing power can be minimised. For example, the maximum amplitude difference may be used to identify the R-peak while the gradient of the amplitude changes may be used to identify the P-wave or T-wave.

The primary purpose of the time window is to isolate the sampled data associated with a given heartbeat so as to separate the ECG signals from different heartbeats (see e.g. FIG. 1). The width of the time window is variable and the processor can be programmed to apply any suitable size of window. Preferably the time window is sufficiently wide to capture up to all of the data sampled from the ECG signal generated by a given heartbeat, but not so wide as to include overlapping data from adjacent heartbeats. The processor may be programmed to apply a time window that is smaller than the whole ECG signal associated with a heartbeat, e.g. so as to focus in on one or more portions of the signal. However it is preferable that the time window is not too narrow so that it can include a number of sampled data points and therefore amplitude changes in the window can be accurately measured. The time window may have a width of at least 5 ms, 10 ms, 20 ms, 30 ms, 40 ms, 50 ms, 60 ms, 70 ms, 80 ms, 90 ms, or 100 ms. The time window may have a width of up to 500 ms, 600 ms, 700 ms, 800 ms, 900 ms, 1 s, or any width matching the R-R interval of a given ECG signal. For a typical adult resting heart rate of 60 bpm the R-R interval is around 1 s. Within the time window, the data is preferably sampled at a high enough rate to provide good resolution of the amplitude and time values, for example at at least 100 Hz and preferably around 1 kHz (as will be discussed below). A sampling rate of 1 kHz provides a time resolution of 1 ms, which is more than adequate for a time window of, say, 80 ms applied to identify the QRS complex in an ECG signal for an adult subject being monitored at rest. The time window may be made shorter for subjects that are moving or undertaking physical activity, and for children, to account for a shorter ECG signal.

This data processing regime has several advantages. Firstly, by translating a feature of interest once it has been found to a single time or amplitude value the bandwidth required for transmission can be kept to a minimum. The device provides security because the key data that is identified is then transmitted as a raw time or amplitude value. Such values will not be meaningful if intercepted without knowledge of the program that is being run by the processor in the device. Furthermore, the processing carried out by the device does not go beyond identification of a particular amplitude or time value, e.g. the clinical significance or otherwise of the key data is left for evaluation after transmission. Subtleties contained in the ECG signal may therefore be preserved. There are also benefits in terms of data integrity and enabling checks to be made outside the device based on the key data in its raw form. The device may comprise a data storage means connected to the processor for local storage of the key data, for example as a back-up if there is a problem with wireless transmission.

The processor may be programmed to run one or more "identification" algorithms that seek to identify a particular pre-defined feature of interest in the ECG signal generated by each heartbeat. Each feature may be represented by key data in the form of a time and/or amplitude value which can then be transmitted for further analysis. The identification of the key data may be carried in the time domain or the frequency domain. For example, if the time window is made relatively large so as to capture substantially the whole ECG signal generated by a heartbeat then the sampled data can be transformed into the frequency domain before looking at the amplitude changes. However, if seeking to provide a time value corresponding to a pre-defined feature then the processor may need to transform back into the time domain before outputting that part of the key data. Processing in the time domain may therefore be more straightforward, although the processor can be programmed to carry out either time or frequency analysis, as desired.

In preferred embodiments the device can be programmed so as to identify certain features that are of interest for a particular patient wearing the device. The processing carried out by the device can therefore be made patient-specific, or condition-specific e.g. for stroke monitoring. Such programming may be carried out before the processor is sealed into the device, especially if the processor is re-used in the manufacture of re-furbished devices as described in the Applicant's co-pending application, published as US 2014/0031663 A1.

In a preferred set of embodiments the processor in the device can be re-programmed during use to change the characteristic and/or other pre-defined features that are to be identified. The processor may be programmed to run a particular algorithm selected from a number of programs stored in a local memory. Alternatively, or in addition, the processor may be programmed via the wireless transmission link, for instance a new program may be downloaded onto the device from a remote controller or gateway device (see below). It may therefore be possible to dynamically program the device while it is being worn by a patient, e.g. changing the content of the key data in response to changes in the patient's condition or because medical personnel wish to select one or more particular features of the ECG signal to monitor.

Some further examples of the key data that may be extracted from an ECG signal are given here, each of which may be identified alone or in combination through appropriate programming of the processor. It will be appreciated that a clinical evaluation may rely on the analysis and comparison of more than one feature.

In one example, the key data comprises the temporal position and/or amplitude corresponding to the P-wave. An absence of the P-wave, together with a general fibrillation, strongly indicates atrial fibrillation, a causal factor in around a third of all strokes (and those with the poorest outcome for sufferers). Another clinical evaluation might look at amplitude variations in the P-wave, such as a sawtooth form, that indicate atrial flutter.

In another example, the key data comprises the temporal position and/or amplitude corresponding to the T-wave. A depressed T-wave may be a sign of myocardial ischaemia.

In another example, the key data comprises the amplitude of the S-T segment of the ECG signal. An elevated S-T segment may be associated with myocardial infarction, acute pericarditis and left ventricular aneurysm.

In another example, the key data comprises the temporal extent of the Q-T interval. A shortened Q-T interval, in combination with a widened T-wave, is usually a sign of hypercalceamia (elevated calcium in the blood) and may be associated with sudden cardiac death, most likely due to ventricular fibrillation. A lengthened Q-T interval due to hypocalceamia indicates a propensity to ventricular tachyarrhythmias that may lead to syncope, cardiac arrest or sudden death. This is of particular importance in pediatric patients.

It has been recognised that the accurate identification of many features in the ECG signal relies on amplitude measurement, but it may not be possible to measure an absolute amplitude value. In fact the baseline amplitude level constantly and normally shifts for various reasons, particularly for ambulatory subjects (so-called baseline wander). It is therefore preferable that the processor simultaneously performs amplitude calibration. For example, the processor may be programmed to perform a statistical analysis of the detected amplitude value for peaks in the signal, and to set a threshold amplitude that is independent of the baseline amplitude level (and shifts in that level). Such analysis may be carried out intermittently, but preferably the calibration is continuous or near-continuous. This allows the processor and its identification algorithm(s) to dynamically adapt to changes to the ECG signal in real time e.g. due to movement of the subject being monitored. This feature can be important when measuring a R-S amplitude value that is then used (preferably externally of the device) to calculate clinical parameters such as heart rate variability and/or respiration rate, as will be described below.

In order to simplify the transmission of key data from the device, each key data point is preferably output as a single time and/or amplitude value. Such values can be output as only a few bytes of data. Preferably the processor is programmed to identify a limited number of key data, for example only one, two, three or four different time and/or amplitude values. This keeps the message size for transmission to a minimum and reduces the bandwidth required. For example, a transmission message for R-peak data may only comprise two pieces of key data: the R-peak time stamp (e.g. 4 bytes) and the R-S amplitude (e.g. 2 bytes). For messages relating to features other than the R-peak, the data bytes may instead be used to send other amplitude and/or time values. The key data may be labelled by a tag e.g. having a size of 1 byte. The data message for each heartbeat can then be reduced, for example, to a size of only 8 bytes.

In some embodiments the key data may comprise information other than the time stamp (or a calculation of heart rate), alternatively or in addition. The data processing means may apply a more complicated algorithm to calculate the heart rate variation (HRV). However it is preferable that the HRV is calculated outside the device, e.g. in a gateway device as will be described below.

HRV may be calculated using time or frequency domain processing (or some combination of both). The Applicant has appreciated that an HRV analysis makes it possible to measure a subject's respiratory rate (RR) indirectly from the cardiac rhythm, sometimes called derived respiratory rate (DRR). For example, known algorithms can use the ratio of the time between a pair of R-R peaks and the successive R-R peak, together with time and/or frequency domain processing combined with the associated amplitude of the R peaks, to calculate the number of breaths per minute. Whereas, conventionally, respiration monitoring is achieved directly by spirometers or nasal thermocouples, or indirectly by transthoracic impedance or strain gauge measurement of chest circumference. Furthermore, the derived RR data may be combined with HR data and both transmitted together as key data. Knowledge of respiratory patterns can be clinically useful where the ECG is continuously or routinely monitored; for instance, the clinical significance of certain cardiac arrhythmias can be more easily understood with reference to respiration. By way of example, apnea may be associated with tachycardia, increased ventricular ectopy or asystole, whereas congestive heart failure and chronic lung disease may result in both tachypnea and tachyarrythmia.

Thus in one set of embodiments the key data comprises a measurement of both heart rate (HR) and data relevant to respiratory rate (RR). Such calculations are made possible by the processing power of the data processing means, based on suitable algorithms. This feature may be considered novel and inventive in its own right, and thus when viewed from a further aspect the present invention provides a cardiac monitoring device comprising means for measuring ECG signals, data processing means arranged to process the ECG signals to provide key data comprising heart rate (HR) and at least one of heart rate variability (HRV) or respiratory rate (RR), and means for wirelessly transmitting the key data from the device.

It will be appreciated that devices according to the this aspect of the invention may not necessarily process ECG signals relating to every heart beat as this is not essential to calculating at least the average heart rate and, in addition, heart rate variability (HRV) and/or respiratory rate. However, it is preferred that ECG signals are continuously or near-continuously received by the processing means and each ECG signal associated with a heartbeat is processed to provide the key data, as is described above with respect to the previous aspects of the invention, so as to maximise the accuracy and information content of the key data. In order to reduce the amount of data transmitted and analysis required remote from the device, the key data preferably comprises heart rate (HR) and respiratory rate (RR), wherein the respiratory rate is preferably a derived respiratory rate (DRR) derived from a heart rate variability (HRV) analysis. The key data provided by the monitoring device can be comparable to that obtained from standard bedside monitoring equipment requiring attachment to the subject.

According to the aspects of the invention defined above, the key data that is made available as a result of the data processing taking place in the device can simplify the data acquisition and display means of a receiver associated with the wireless transmitter. In the monitoring device the wireless transmitter or transmission means is preferably arranged to transmit the key data (and any other data) to a receiving means comprising a display and a user interface (e.g. handheld, mobile or desktop device). The receiver may do no more than display the actual HR (and, optionally, RR data) made available by the device. The associated receiver may be any hand held, mobile or desk top device such as a smart phone, laptop, netbook or PC. Thus according to the invention there can be delivered direct to a clinician meaningful data which does not require any further analysis. However, as was mentioned above, there can be a benefit in reducing both the data processing and transmission power required by identifying time and/or amplitude value(s) corresponding to one or more feature(s) of the ECG signal and then transmitting those raw values as key data for subsequent analysis in the receiving means or beyond.

The receiving means may be connected to a database or electronic patient record system. The receiving means may be arranged to receive data from one or a number of monitoring devices. The invention therefore extends to a remote monitoring system comprising one or more cardiac monitoring devices according to any aspect of the invention, one or more receivers each wirelessly connected to one or more of the monitoring devices, and data display and/or storage means associated with the receiver(s).

The monitoring system preferably takes the form of a distributed network comprising a plurality of monitoring devices. Each of the monitoring devices may be wirelessly connected directly to a receiver provided by a central server. The server may provide a central data display and/or storage means. The server may also carry out further analysis based on the key data that it receives, for example calculating heart rate and/or respiration rate that can be output to a display. A number of monitoring devices, whether associated with the same or different subjects, can be connected to the same server. The server may output patient-specific data via a wireless link to display units or browser-enabled devices, such as a smart phone or tablet carried by a clinician.

If the monitoring devices are worn by a number of different patients then it can be preferable that data relating to each patient is kept separate. Especially when the key data transmitted by the monitoring devices is raw data that is preferably further processed or analysed before being displayed and/or stored, it can be preferable for the monitoring device(s) worn by a given patient to transmit to a dedicated gateway device rather than to a central server in the network. Thus in a preferred set of embodiments the distributed network comprises a plurality of receivers, preferably each of the receivers comprising a network gateway device connected to the central server. Each network gateway device is preferably paired with the monitoring device(s) worn by a particular subject. In other words, it is preferable that the network gateway device is arranged to receive wireless transmissions from one or more cardiac monitoring devices only if they are identified as being associated with a given subject. It is understood that a particularly robust ECG evaluation system for a given subject preferably comprises at least one of the monitoring devices as outlined above in combination with a dedicated gateway device that is arranged to receive the key data as transmitted by the wireless transmitter. The gateway device may comprise a suitable wireless receiver.

It will be appreciated that more than one monitoring device may be paired with the gateway device. For example, the gateway device may be arranged to receive key data from multiple devices that are mounted in different positions on a subject or from different devices that are programmed to look for different features in the ECG signal. The gateway device may be further arranged to receive wireless transmissions from one or more other monitoring devices associated with the subject, such as a blood oxygen monitor. The pairing of the gateway device can be controlled by arranging the gateway device to receive identification information relating to each monitoring device for which it is to receive wireless transmissions and/or relating to the subject being monitored. It is advantageous that the gateway device is exclusively allocated to a particular subject, so that all data received at that device relates to the same person. The gateway device may comprising a data storage means to provide local storage and a back-up to any central server.

In one set of embodiments, each network gateway device preferably comprises a processor that is programmed to analyse the key data that it receives. Where the key data comprises at least the timestamp of the detected R-peaks, then the gateway processor can calculate the heart rate. The gateway device can provide an output comprising heart rate and, in addition, preferably comprising one or more further clinical parameters such as respiration rate or a parameter relating to a pre-defined feature of interest in the ECG signal. For example, the respiration rate can be calculated by analysing the temporal variation of the R-S peak amplitude, using an amplitude modulation or frequency modulation algorithm. In another example, the gateway device may output a warning when the amplitude value of the P-wave drops below a certain threshold indicative of atrial fibrillation and the potential risk of stroke. It can be particularly advantageous for the gateway device to process the data that is incoming from a number of different cardiac monitoring devices connected to a subject in different lead positions, as different features of the ECG signal may be better observed in other lead positions than the commonly used Lead I position.

The key data received by the gateway device can be forwarded to a central server in the network, for the purposes of integrity, even though analysis is carried out by the gateway device. The gateway device may comprise a data storage means for local back-up.

In another set of embodiments, each network gateway device may function solely to manage the data being received from a subject's monitoring device(s) and to forward this data to a central server in an appropriate fashion. The gateway device may also send an output to a display unit or browser-enabled device e.g. handheld wireless smart phone or tablet. If the processing carried out in the cardiac monitoring device has already calculated the heart rate, for example, then this can be displayed directly to clinicians without any further processing being required.

While a networked system of gateway devices can be particularly suitable for managing key data, especially raw data, that is wirelessly transmitted for a number of subjects being monitored, the Applicant has recognised that a patient-specific system architecture can provide benefits in any distributed health monitoring situation. Thus when viewed from a yet further aspect the present invention provides a health monitoring system comprising a plurality of health monitoring devices, at least one of the devices being wearable by each of a respective plurality of subjects being monitored, and a corresponding plurality of network gateway devices, with each of the network gateway devices being arranged to wirelessly pair with the monitoring device(s) identified as being associated with a given subject being monitored. It is seen that each gateway device is arranged to exclusively receive wireless transmissions from a given subject's monitoring device(s). Each of the plurality of network gateway devices may be connected to a central server by an internet connection, either ethernet or wireless.

To ensure that each gateway device is exclusively paired with the monitoring device(s) for a given subject, it may be arranged to receive identification information relating to the monitoring device(s) with which it is to pair and/or relating to the subject being monitored. Such identification information may be directly input to the gateway device (e.g. by a local user), but preferably the gateway device serves only as a data display and/or forwarding unit without allowing any user input. Rather it is preferred that the gateway device receives the identification information from a central server. The server may also provide configuration information relating to a particular monitoring device to the gateway device so that it not only knows to connect to certain identified monitoring device(s) but also knows what to expect to receive from the device(s) e.g. the type of key data being transmitted. The server may act to reconfigure the gateway device at any time, e.g. to disconnect from a particular device and connect to another. Preferably the gateway device displays an output that identifies the monitoring device(s) connected thereto.

There will now be described some preferred features that are applicable to all aspects of the invention outlined above.

The cardiac monitoring device may be mounted or affixed to a subject by any suitable means. However, due to the integrated nature of the device with the data processor sealed inside the substrate, it is particularly suitable for use as a self-adhesive monitor rather than as a monitor that is held in place by a chest strap or other mounting means. According to a set of particularly preferred embodiments the means for measuring ECG signals comprises at least two electrodes for making electrical connection to the skin of a mammalian subject, and self-adhesive means for attaching the substrate to the subject. In one set of embodiments the substrate comprises a laminated structure which has the data processing means embedded between a pair of layers thereof.

The means for measuring ECG signals preferably comprises a pair of electrodes, commonly known as an ECG "lead". Any lead position may be used, depending on the angle at which it is desired to view the heart. However, as is mentioned above, certain feature(s) to which the key data relate may be better observed in a particular lead position and the attachment of the device can therefore be chosen depending on the key data that is to be extracted from the ECG signal. In Lead I position, for example, the electrode pair is positioned across the chest from right arm (RA) to left arm (LA) so as to measure the voltage difference between the RA electrode and the LA electrode. However the Applicant has appreciated that integrated cardiac monitoring devices in accordance with the invention may be particularly useful for making multi-lead ECG measurements, for example by affixing two or more of the devices at different lead positions on the body. Thus a Lead II measurement could be made by positioning one device in the right arm (RA) position and another device in the left leg (LL) position, while a Lead III measurement could be made by positioning one device in the left arm (LA) position and another device in the left leg (LL) position. More complex lead positioning, such as 3-lead, 5-lead and 12-lead ECG monitoring, could be carried out using multiple devices. Thus the invention may also extend to a cardiac monitoring system comprising a plurality of the cardiac monitoring devices attached to a subject in different lead positions. In such a system it is preferable for the devices in their different lead positions to be paired with the same gateway device that is allocated to the subject being monitored. A relatively sophisticated output can then be provided from analysing the key data collected in the different lead positions.

It will be apparent from the discussion above that the sampling rate, that is the frequency at which the processing means samples the received ECG signals, can be important in determining the type and/or accuracy of the key data provided by the device. In order for each ECG signal associated with every heartbeat to be sampled, the sampling rate must be at least of the order of a slow heart rate e.g. 60 bpm or 1 Hz. For the key data to provide heart rate alone it may be sufficient for the sampling rate to be around 1-10 Hz. Standard wired ECG monitors typically sample at 125-250 Hz. However, the Applicant has recognised that it is desirable for the processing means to be able to apply a much higher sampling rate to an ECG signal than is conventional, so as to achieve a greater accuracy in determining the positions of the R peaks and resolving other features of interest in the ECG signal. In a preferred set of embodiments the processing means digitises the received ECG signals at a rate of >250 Hz, and further preferably at a rate >500 Hz, >750 Hz, or around 1 kHz. The higher accuracy provided by this increased sampling rate offers greater scope for the application of quantitative HRV analysis, where temporal variations in the order of a few milliseconds or less are of significance. Such sampling rates may be achieved, for example, in a 32 bit microcontroller, preferably provided on a chip, such as the EFM32 available from Energy Micro. Thus in a preferred set of embodiments the data processing means comprises a microcontroller.

As is mentioned above, an important advantage of the invention is that the entire ECG signal peak is not necessarily transmitted wirelessly from the device as the data processing means extracts key data such as heart rate (HR), or heart rate (HR) and respiratory rate (RR)/heart rate variability (HRV), or key data comprising the temporal position of the R-peak and at least one time or amplitude value associated with another feature of interest in the ECG signal. It will be appreciated that other key data may be extracted from the ECG signal as well. The device can thus benefit from lower data transmission rates and lower bandwidth requirements than previously known. In a set of embodiments the device operates in a first mode of operation wherein only the key data is made available. This corresponds to a low power mode of operation that reduces the power consumption of the wireless transmitter and thus can prolong battery life. In this mode of operation the data processor may sample the data received from the ECG signals at a rate lower than the digitization rate, so as to save power. For example, the processor may only sample one in four of the digitised data points. This may be enough to generate accurate key data while still maintaining capacity for higher accuracy processing where necessary or desirable.

Although in one mode of operation the device prepares and transmits key data relating to the measured heartbeats, the device may operate in another mode of operation wherein the raw data from the measured ECG signals is provided to the wireless transmitter. In such a mode of operation there may be little or no burden on the data processor but a larger bandwidth may be required to transmit the data. The raw data may, for example, comprise a time interval measurement (e.g. R-R time interval) and/or an amplitude measurement (e.g. R-S amplitude) for the ECG signal associated with a heartbeat. The device may switch into such a mode of operation from time to time, for instance on demand, so that the raw data can be used for purposes including calibration, error-checking and/or debugging. However, as is described above, when the processor is programmed to apply a time window to the sampled data and measure the amplitude changes in the window, the amplitude changes can be used to identify key data in the form of time and/or amplitude values that is a sub-selection of the raw data sampled from the ECG signal. Such key data can be extracted continuously and transmitted from the device in a constant mode of operation without representing a large data load and power consumption.

In one or more modes of operation the device may make available other data from an ECG signal, such as measurement of the ECG signal waveform, in addition to or instead of the key data. Thus in another, not mutually exclusive, set of embodiments the device operates in a second mode of operation wherein a measured ECG signal waveform is made available. In this second mode of operation the measured ECG signal waveform may be transmitted independently or together with the key data. Although this corresponds to a higher power mode of operation, the full ECG signal may be required at certain times, for example when setting up, for calibration, and/or when a full waveform view is desired for clinical analysis. The device may switch between the first and second modes of operation on demand. Preferably the first mode of operation is the default mode so as to minimise power consumption. However the device may be arranged to temporarily switch into the second mode of operation at programmed intervals, for example once every 10 minutes or once an hour, so as to provide a snapshot of the ECG signal waveform.

In some embodiments the device may be instructed to operate in such a second mode of operation (in which the measured ECG signals are provided to the wireless transmitter for transmission) as a result of an analysis of the key data. The analysis of the key data, either carried out by the processor in the device or externally of the device, may indicate that there are some features in the ECG signal that should be viewed in more detailed, e.g. by a skilled clinician studying the ECG waveform and/or by further analysis being carried out. The device or a monitoring system comprising the device may therefore elect to switch into a mode that transmits the full ECG signal when there is found a particular need to do so.

Another piece of data that may be transmitted from the device in addition to the key data extracted from the ECG signal is an indication of the current battery voltage or remaining battery power.

The Applicant has recognised that is it desirable to minimise the power consumption of the device, especially if it is a single-use device containing an integrated battery and thus having a finite lifetime. However low power consumption is desirable even if the device is rechargeable, so as to prolong its period of use and to provide for uninterrupted subject monitoring. In addition to providing a low power, first mode of operation as described above, it is preferable for the device to also provide a standby, third mode wherein substantially no power is drawn by the processing means. Thus in a set of preferred embodiments the processing means is arranged to switch the device into a substantially zero power mode when no ECG signals have been measured and received for a certain time period, e.g. 10 minutes. Thus the device can detect itself when it is not in use, e.g. not attached to a subject, and switch into a standby mode of operation. The wireless transmitter may be arranged to transmit a signal indicating when the device is switching into a standby or sleep mode.

Additionally or alternatively, the device may comprise attachment sensing means to give an indication of whether or not it is attached, or properly attached, to the subject. This could, for example, prevent operation of the device unless attachment is detected, to avoid operating the device inadvertently or to avoid erroneous results being obtained by operating the device when it is not properly in contact with the subject. Attachment may be sensed by a physical sensor, such as a contact sensor, or from the data collected by the data processor, e.g. by analysing the signal-to-noise ratio to determine when the device is not properly attached to a subject. The data processing means may use such an attachment sensor to determine when to switch in and out of a zero power or standby mode of operation.

In a preferred set of embodiments the wireless transmitter is arranged to transmit the key data (and any other data) to a suitable remote receiver. This could allow the periodic downloading of data when the device is in the presence of, or connected to, a suitable reader, so that real-time communication is not necessary. Data may therefore be extracted from the device on demand. As is mentioned above, the data processing means may comprise an electronic memory for temporary or longer term storage of data therein. The electronic memory may comprise a rewritable memory—e.g. flash memory—in order to allow some degree of re-programming to configure it, to provide software updates, etc.

However the wireless transmitter or transmission means is more preferably configured to permit the regular, frequent or continuous transmission of data. Thus in a set of preferred embodiments the wireless transmitter is arranged to transmit the key data associated with every measured heartbeat on a real-time basis. In another set of embodiments the wireless transmission means is arranged to transmit key data comprising HR and at least one of HRV or RR on a regular basis, such as every 10, 20, 30, 40, 50 or 60 seconds, or every one, two, three, four or five minutes. Alternatively, messages containing key date in the form of time and/or amplitude values may be transmitted regularly, on a near-continuous basis, as the key data is extracted from every heartbeat. Such messages may be transmitted at a rate of 1, 2, 3, 4, 5 or up to 10 Hz. An electronic memory may not then be required, although it may still be provided for data back-up purposes.

In a set of preferred embodiments, the wireless transmitter comprises a radio transmitter. An example of a suitable radio transmitter is the ANT wireless transceiver designated AP2 which is available from Nordic Semiconductor ASA. Although the ANT wireless protocol is one preferred low power protocol that employs relatively low data rates, the wireless transmitter may employ any suitable protocol for data transmission. For example, the wireless transmitter may use Bluetooth™ technology.

The wireless transmitter or transmission means may make the key data (and other data) available to any receiver within range e.g. 5 m. However it is preferred that the transmitter connects to an associated receiver, for example provided by an associated gateway device, so as to ensure that data is only transmitted to the intended receiver and to avoid cross-talk where the data from one subject may be confused or interchanged with that from another. This enhances system robustness and safety. If a Bluetooth™ wireless protocol is used then this may correspond to device pairing. The wireless transmitter is preferably arranged to connect with an associated receiver upon activation of the device. Where the device is provided with an attachment sensor, as mentioned above, this may provide the transmitter with an instruction to find and connect to a receiver.

The wireless transmitter may employ any suitable protocol for data transmission. As mentioned above, the ANT wireless protocol is one preferred low power protocol that employs relatively low data rates. In order to minimise power consumption the wireless transmitter preferably transmits a message for each heartbeat. The message contains at least the key data relating to the heartbeat. Other data may also be provided in at least some of the messages. With the ANT message protocol it has been found that a message containing 8 bytes of data can be sufficient to transmit the key data. Preferably each message comprises a message identifier or 'tag'. The message identifier may be a sequential number so that missing data is easily detected and can be ignored or interpolated. Each message may comprise a header specifying the message type, for example specifying an error message instead of a data message. Other message types may be used to signify the commencement and/or termination of a message stream.

The Applicant has devised several ways to ensure that transmission of the key data is reliable. Firstly, in a set of preferred embodiments each transmission comprises a pair of messages, one message corresponding to the last heartbeat and the other message corresponding to the previous heartbeat. By repeating each message twice, any one-off errors in the key data may be detected and optionally corrected. Secondly, in the same or another set of preferred embodiments the transmitter waits for an acknowledgement of each transmission or message being received. The transmitter than then hold the message(s) and re-transmit until acknowledgement is received or timed out. These redundancy mechanisms help to minimise data loss and may be used alone or in combination.

While the data processing means is sealed within the substrate of the monitoring device, it may be connected to the means for measuring ECG signals in any suitable way. As is mentioned above, in a set of particularly preferred embodiments the measuring means comprises an electrode assembly comprising at least one pair of self-adhesive electrode pads for attaching the assembly to a mammalian subject. It is further preferable that the electrical connection between the pads and the data processing means comprises at least one extendible electrical connection. The extendible electrical connection(s) between one or both of the electrode pads and/or the data processing means allows relative movement, particularly axial movement, between the electrodes and the rest of the assembly without compromising the integrity of the electrical connection. This is beneficial in allowing a large range of movement of the subject whilst minimising problems associated with the electrode becoming detached or giving inaccurate results given as a result of motion artifacts, such as electrical noise being introduced by movement of the electrode pad relative to the subject's body. Because the electrical connection between the pads is extendible the pads are able to "float" relative to the substrate and move with the body without applying a mechanical stress to the electrical connection. The electrode assembly preferably comprises a laminated structure with the data processing means sealed between two layers thereof. Such an electrode assembly is the subject of the Applicant's co-pending patent application, US 2014/0031663.

It will be appreciated that cardiac monitoring devices according to the invention are not limited to monitoring cardiac function alone and may also monitor other vital signs, using the same or additional measuring means. In some embodiments other sensors than the ECG measuring means may be provided to give further functionality. For example, an accelerometer and/or magnetometer may be provided which would allow the electrode assembly to detect motion of the subject. Such motion detection can be used to remove motion-related artefacts from the ECG signal when monitoring an ambulatory subject.

BRIEF DESCRIPTION OF THE DRAWINGS

Some preferred embodiments of the present invention will now be described, by way of example only, and with reference to the accompanying drawings, in which.

DETAILED DESCRIPTION

Figure 2:
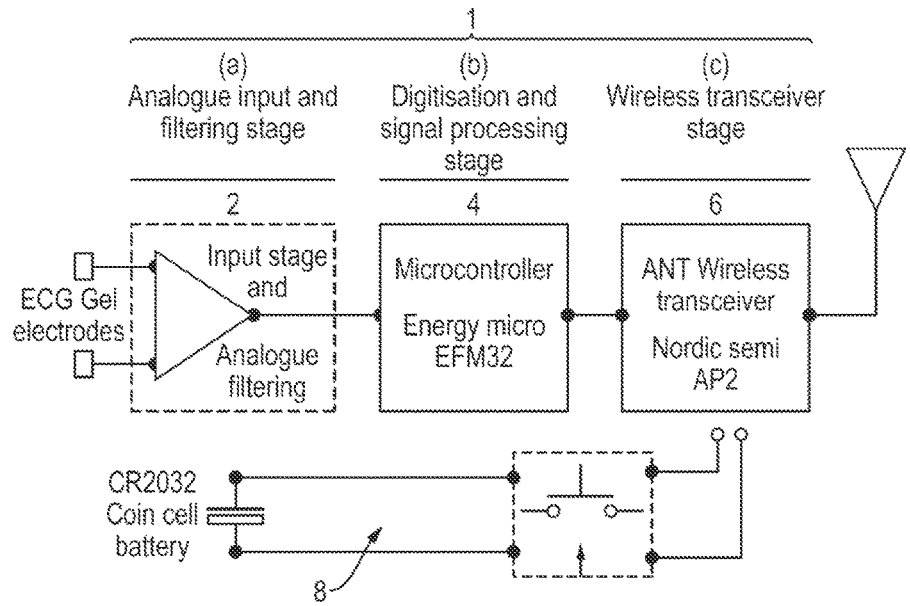
FIG. 2 is a schematic electrical block diagram for a cardiac monitoring device according to an embodiment of the present invention.

In FIG. 2 there is seen a schematic layout of the main electrical components of a cardiac monitoring device 1. The device 1 comprises ECG measuring means 2 including a pair of ECG gel electrodes connected to an input stage amplifier. An analogue ECG signal may be amplified and filtered at the input stage. For example, the millivolt level signal from the ECG electrodes may be amplified while 50/60 Hz induced noise and higher frequency muscle noise is filtered out. The input stage 2 is designed to reduce the effects of motion artefacts and ensures that the device 1 is suitable for ambulatory as well as stationary subjects. The construction of the device 1 is described below with respect to FIGS. 5-8.

Figure 1:
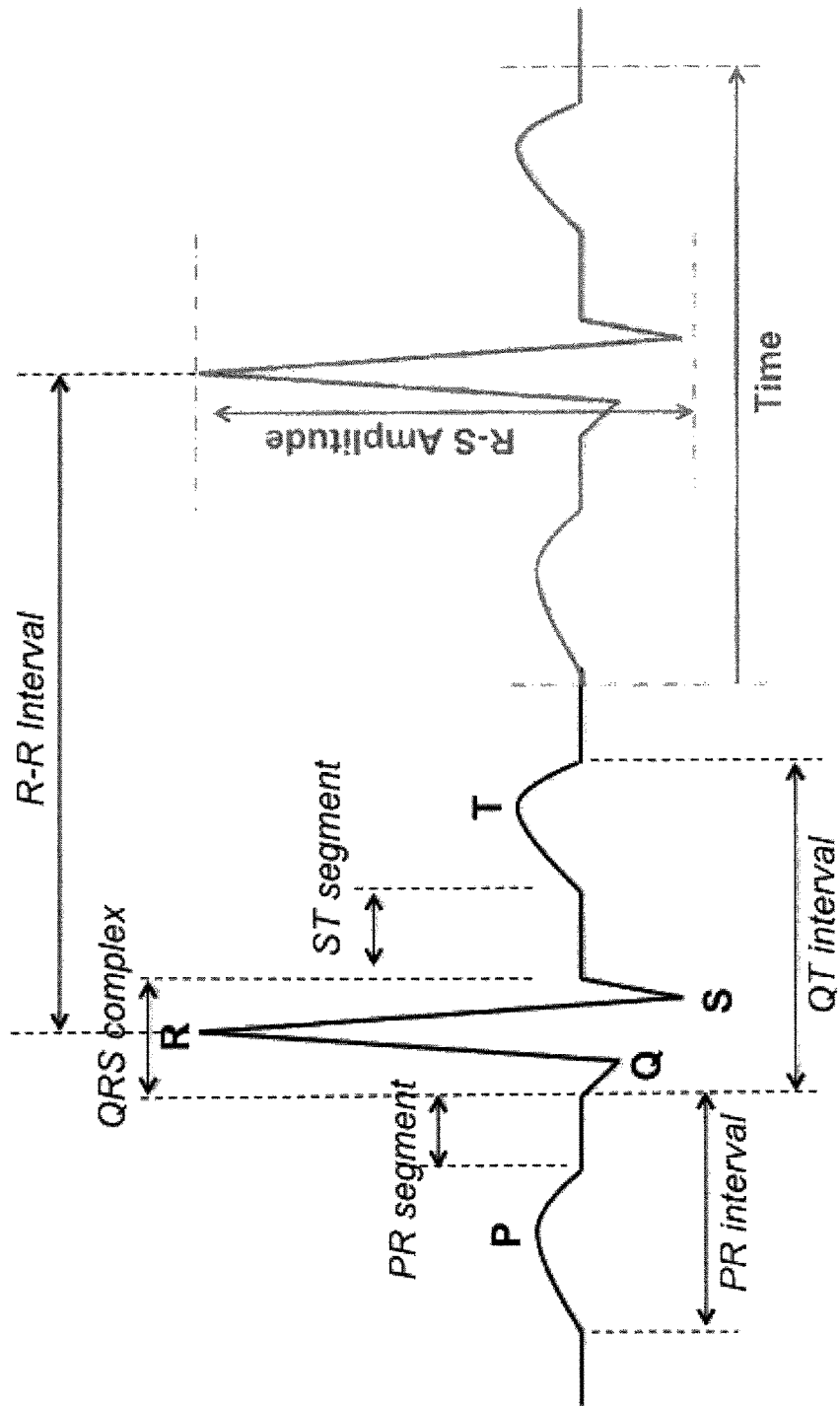
FIG. 1 is a schematic diagram of a typical ECG signal for a healthy adult subject.

The amplified and filtered ECGs signal are supplied from the measuring means 2 to a data processing means 4 comprising a data processor including a microcontroller such as the EFM32 from Energy Micro AS. The microcontroller is designed for very low power operation. The measuring means 2 is connected to the input of an analogue-to-digital converter (ADC) integrated in the microcontroller of the data processing means 4. There the amplified and filtered ECG signals are digitised at 1000 samples per second (1 kHz) and processed so as to extract key data such as heart rate (HR) Or the processor may not go so far as to calculate HR and instead it may run a peak identification algorithm so as to detect the R-peak in the signal (see FIG. 1) and extract key data comprising the time stamp of the peak and one or more other time/amplitude values such as the R-S amplitude. This sampling rate is much higher than standard ECG monitors, which typically sample at only 125-250 Hz. The high sampling frequency enables higher accuracy in determining the positions of the R peaks in the ECG signal. This higher accuracy offers greater scope for the application of quantitative HRV analyses where temporal variations of the order of a few milliseconds or less are of significance.

The key data is passed from the data processing stage 4 to a wireless transceiver stage 6. The wireless transceiver may use the ANT or other wireless protocols. As the ECG signals have been processed and reduced to key data, the wireless data rate and thus the power consumption can be minimised. The device 1 also includes an electrical power supply circuit 8 connected to a coin cell battery. A typical manganese dioxide lithium battery coin cell (CR2032, 3 V, 200 mAh) can provide 25 to 30 hours of continuous operation.

Connection of the cardiac monitoring device 1 in one exemplary remote monitoring system is shown by the schematic overview of FIG. 2. The device 1 transmits key data to a data acquisition platform (DAQ) over a wireless transmission link. The processed data provided by the device 1 is transmitted in the form of messages. According to one possible transmission protocol, a burst message is sent for each heart beat, that is, for each R peak detected in the ECG signal. Each message may be made up of at least three parts: a header, a tag and a key data value. The purpose of the header is to specify the message type, e.g. data message or error message. The numerical tag associated with each message enables successive messages to be uniquely identified and allows the detection of gaps in the message stream. A data message relating to R-peak detection might use 1 byte for the header, 1 byte for the tag, 2 bytes for the amplitude value and 4 bytes for the time stamp, i.e. a total message size of only 8 bytes. For non-R-peak messages the data bytes may be used to send other data and parameters. Another type of message is a battery status message, which may use the tag component to send a single byte that can be converted to a battery voltage value at a receiver.

The monitor 1 extracts the key data from the continuous ECG measurement and only forwards a message to the data acquisition platform (DAQ) when required, namely when each heart beat is detected and the heart rate or other information has been determined. Each burst message contains a message identifier in the form of a sequential number n, n+1, n+2, . . . etc., together with the key data or other data being transmitted. In one example, heart rate (HR) may be derived from the ECG amplitude and time measurements by an algorithm run in the microcontroller and provided as key data. In other examples, as mentioned above, the message may be used to transmit raw data values corresponding to particular time and/or amplitude values identified in the ECG signal. Typically, the ANT wireless message protocol defines a burst message with 8 bytes of data payload, which is sufficient to define the key data for many clinical observations. This guarantees very low power consumption by the wireless transceiver stage 6. For example, at a heart rate of 60 bpm the device 1 sends only one 8 byte message per second—an extremely low data bandwidth—and does not send messages unless there is new data.

In a particularly beneficial message transmission protocol, each wireless transmission comprises two messages. At the start of a message stream a commencement message is prepared by the data processing stage 4 and its tag value is initialized at 0 (in decimal). A data message is then prepared with tag 0 and relayed, together with the commencement message, to the wireless transceiver stage 6. The transmitter stage 6 sends the pair of messages to an associated receiver. For the next heartbeat a second data message is prepared in the data processing stage 4 with tag decimal value 2. Both the first and second data message are sent to the wireless transceiver stage 6. This new message is then transmitted in a pair together with the previous message. The transmission stream continues until the final ith data message is transmitted along with the (i−1)th message. The message stream is competed by a termination message that is sent in a pair along with the final ith data message. By sending each data message twice there is provided a redundancy mechanism that helps to minimise data loss.

Figure 3:
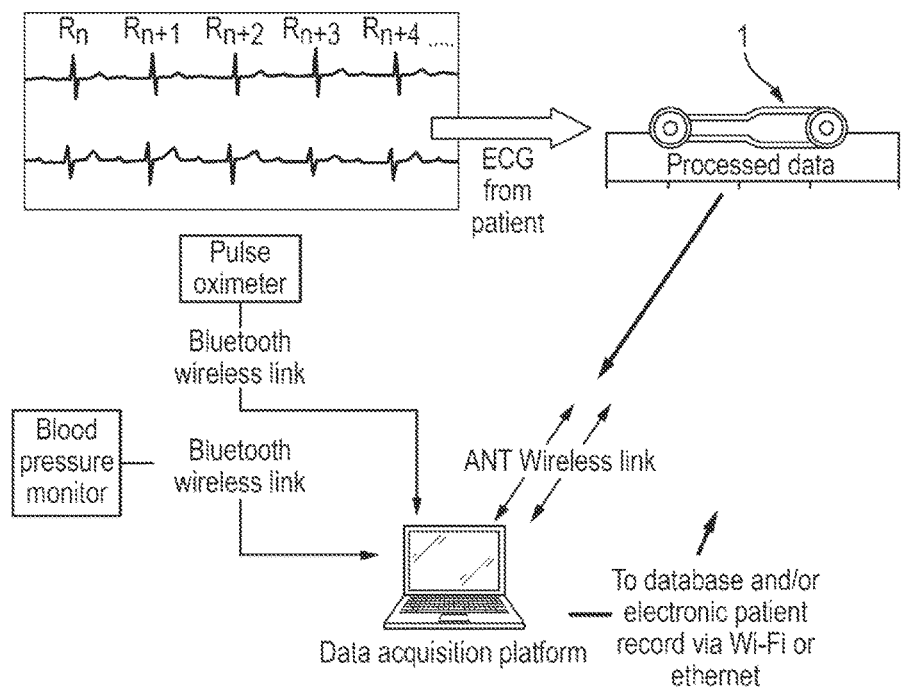
FIG. 3 is a schematic overview of a remote monitoring system including the cardiac monitoring device.

As is shown in FIG. 3, the cardiac monitoring device 1 may be wirelessly connected to a data acquisition platform (DAQ) that also wirelessly receives measurements from other monitors such as a pulse oximeter and a blood pressure monitor. While the DAQ continuously receives data from the cardiac monitoring device 1, it may also receive data quasi-continuously from the other body worn monitors. The DAQ may synchronise all the data received, carry out additional processing where necessary, and forward the data to a data base or electronic patient record. A user interface on the DAQ allows a user to enter patient details and various alerts or alarms for each patient if any of the individual or correlated vital sign values are outside programmed limits.

Figure 4:
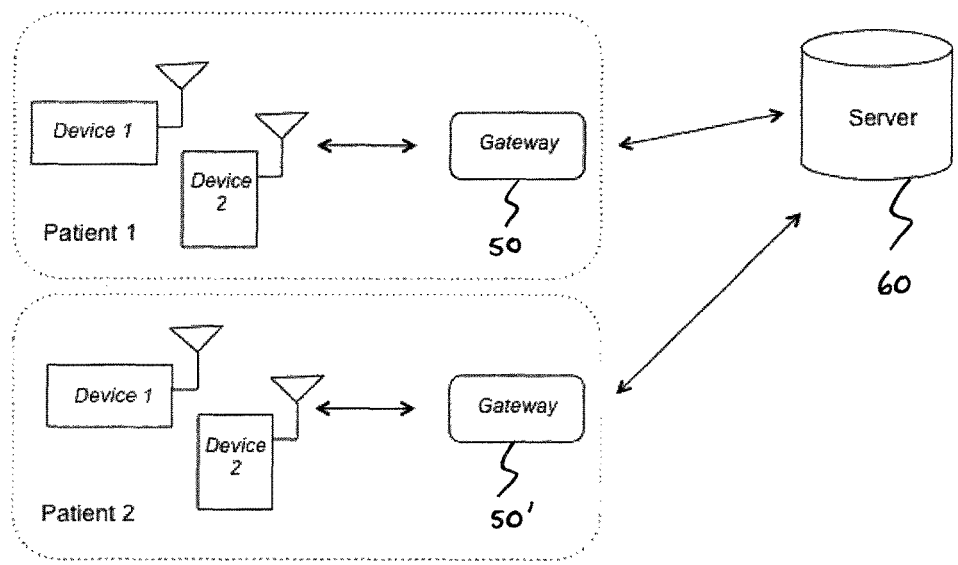
FIG. 4 is a schematic overview of another cardiac monitoring system.
Figure 5:
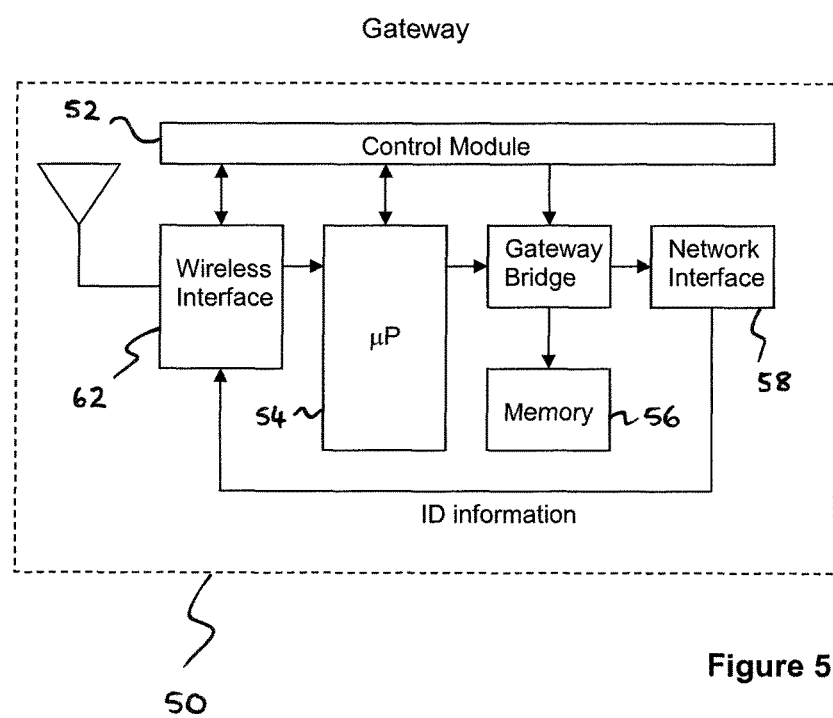
FIG. 5 is a schematic overview of an exemplary gateway in a monitoring system such as shown in FIG. 4.

FIG. 4 provides an overview of a network architecture for a distributed patient monitoring system. Patient 1 is wearing two health monitoring devices, Device 1 and Device 2, that each have a wireless connection with a dedicated patient gateway 50. The patient gateway device 50 may provide an output to a user display (not shown) and is also connected to a central server 60 for the network. Patient 2 is wearing his or her own health monitoring devices, Device 1 and Device 2, that may be e.g. a cardiac monitoring device and another device such as a blood-oxygen monitor. Both Device 1 and Device 2 are uniquely paired with another gateway device 50' dedicated to that patient.

In one example the key data transmitted from the wireless devices to each gateway device 50, 50' may be raw data comprising the QRS time stamp and one or more further amplitude or time values, such as the R-S amplitude value. As is seen from FIG. 5, a typical gateway device 50 comprises a processor 54 that can analyse the key data and calculate clinical parameters such as heart rate and/or respiration rate. These parameters may be stored in the gateway memory 56 as well as being sent via a network interface 58 to the server 60. A gateway controller 52 can dictate the data analysis that is carried out by the processor 54.

The gateway device 50 can receive signals from the network, e.g. sent from the central server 60, via its network interface 58. ID information may be provided that acts to identify the patient for each gateway and the monitoring devices associated with that patient. The ID information is passed directly from the network interface 58 to the wireless interface 62 so as to bypass the gateway controller 52 and ensure that the gateway device is exclusively paired with the monitoring device(s) relating to a given subject. Configuration information may also be provided to the gateway device 50 which relates to the data expected to be received at the wireless interface 62. The processor 54 can be dynamically configured (and re-configured) to analyse the received data based on the configuration information.

Figure 6:
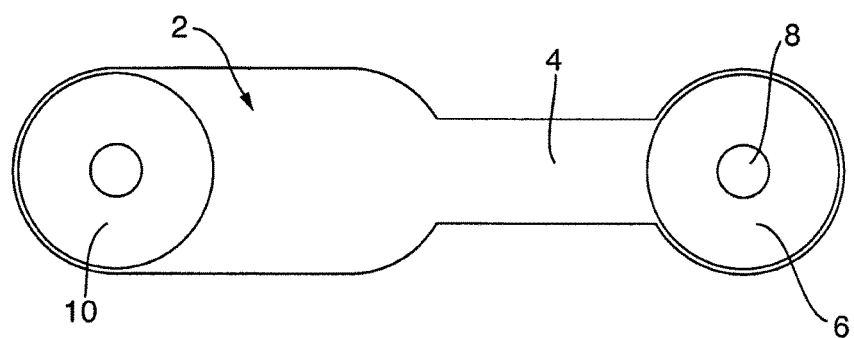
FIG. 6 is a view from beneath of an electrode assembly for the cardiac monitoring device.
Figure 7:
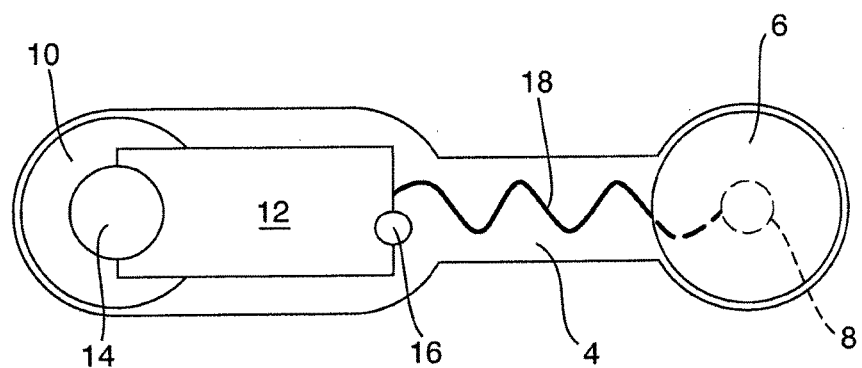
FIG. 7 is a view of the electrode assembly of FIG. 6 from above with the upper layer removed.

An electrode assembly for the cardiac monitoring device 1 is shown in FIGS. 6 and 7. The electrode assembly is based around a substrate 2 which is, for example, made of a laminate comprising a medical grade polyurethane foam layer on the base onto which is sealed a polyethylene sealing layer (omitted from FIG. 6 for clarity). The laminar construction is seen more clearly in FIG. 8. The substrate 2 has a narrowed portion 4 between the wider part of the substrate and a bulbous end to which is mounted a standard ECG gel electrode module 6, having a central electrically conductive portion 8 surrounded by adhesive. A similar electrode module 10 is provided at the other end of the substrate. The electrode modules 6, 10 are available as standard parts, pre-approved for human medical use. As these are the only parts of the assembly to contact the subject directly, no additional approvals for direct physical contact are required for the rest of the assembly.

Sandwiched between the two layers of the substrate 2 are an electronics module 12, a button cell battery 14, a push button 16 and a connecting wire 18. The connecting wire 18 makes an electrical connection between the conducting portion 8 of the first electrode module and the electronics module 12. It may be seen that the connecting wire 18 has a serpentine shape allowing it easily to extend or contract along the axis of the substrate 2. This allows the whole assembly to be bent or stretched in any direction without causing strain on the electrical connection, potentially compromising the integrity of the connection or the security of adhesion to the patient's skin. This flexible arrangement gives a more reliable electrical signal from the electrode, which can in particular aid accurate measurement of signal amplitude values for calculating parameters such as the respiration rate, as well as enhancing the wearer's comfort.

The second electrode module 10 is connected directly to the electronics module 12, as is the button cell battery 14 and the push-button 16. The electronics module 12 is provided on top of the second electrode module 10 so as to improve its mechanical stability. The electronics module 12 includes a microprocessor and a short-range radio transmitter allowing the assembly to transmit data to a suitable receiver. The push-button 16 is of the momentary action type and is arranged initially to apply power from the circuit 12 to initialize it and to maintain the power supply. This allows for long shelf life since the battery is not drained until it is required after being switched on.

Figure 8:
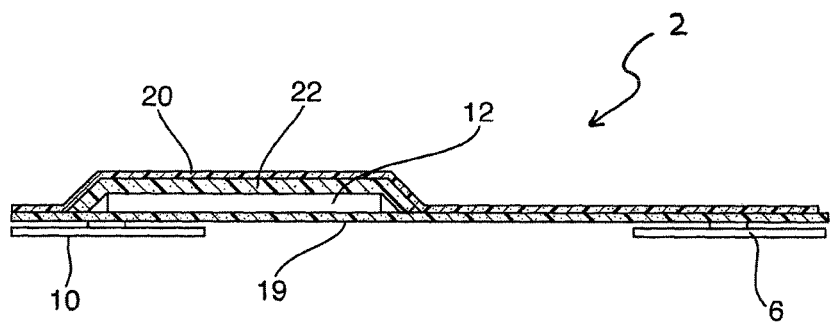
FIG. 8 is a schematic cross-sectional view taken vertically through the electrode assembly of FIGS. 6 and 7.

FIG. 8 gives a schematic cross-section through the electrode assembly shown in FIGS. 6 and 7. From this it may be seen that the substrate 2 comprises a flexible base layer 19 e.g. of polyethylene foam to which the two standard ECG electrodes 6, 10 are attached. Laminated to the other side of the base layer 19 is a sealing layer 20 of polyurethane foam. An air-tight pocket is formed between the base layer 19 and the sealing layer 20 and this accommodates the electronics module 12 and optionally a further padding layer 22, also of polyurethane foam. The electronics module 12 is thus sealed within the substrate 2.

In use the device is switched on by pressing the button 16 and is then attached to a subject by means of the self-adhesive electrode modules 6, 10. Because both the electrode modules 6, 10 and the substrate 2 are made of medical grade polyurethane foam, the assembly meets approval for human use. The device is relatively insensitive to its precise placement on the body, although a position that approximates the Lead I position (Left Arm/Right Arm) may be used for the convenience of clinical staff. More than one device may be positioned on the body so as to provide multi-lead ECG measurements. For example, a Lead II measurement may be made by positioning one device in the right arm (RA) position and another device in the left leg (LL) position, while a Lead III measurement may be made by positioning one device in the left arm (LA) position and another device in the left leg (LL) position. More complex lead positioning, such as 3-lead, 5-lead and 12-lead ECG monitoring, could be carried out using multiple devices positioned on the body. In a default mode of operation the device (or each device) will then periodically transmit data relating to the subject's cardiac rhythm. Once the electrode assembly is no longer being used for a particular subject, or once the battery 24 is exhausted, the device may be removed and sent for recycling.

To recycle the device 1 the two layers are partially separated at the left hand end (as viewed from FIGS. 6 and 7). A line of weakness of other frangible portion may be provided on one or both layers to facilitate this. The battery 14, electronics module 12 and push button 16 may then be removed by pulling them out of the device. Again a frangible or otherwise separable connect between the electronics module 12 and the electrode module 10 and connecting wire 18 may be provided to facilitate this. Once removed, the battery 14 can be recharged, or recycled using standard facilities, and the electronics module 12 and button 16 can be re-used in the manufacture of further devices. The remainder of the device, i.e. the substrate 12 and electrode modules 6, 10 that came into contact with the subject, is disposed of using suitable medical waste protocols. The electronics module 12 and button 16 may be cleaned and sealed inside the two layers of a substrate in a new device, which may then be sterilised ready for re-use.

Figure 9:
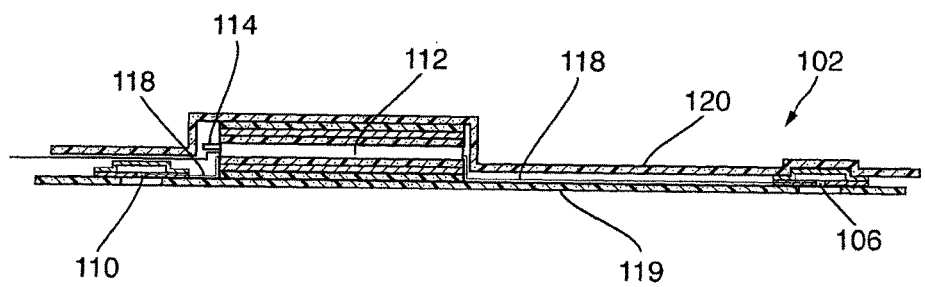
FIG. 9 is a schematic cross-sectional view of another sensor assembly.

FIG. 9 shows a schematic cross-section through the electrode assembly of a device having a slightly different structure. It may be seen that, as before, the substrate 102 comprises two carrier layers 119, 120 e.g. made of polyurethane foam that are laminated together to enclose the functional components of the device, namely a pair of electrode connectors 106, 110, an electronics module 112, an extendible connecting wire 118 and a battery in a holder 114. The device is designed such that assembly can be achieved quickly and easily by hand. Furthermore, after use the functional components can be removed by pulling open the laminated substrate. While the electrode connectors 106, 110 and associated gel pads that have been in physical contact with a patient may be discarded, the battery 115 and electronics module 112 can be re-used or recycled. In particular, a refurbished device can be made by incorporating the electronics module 112 into a new substrate.

The description above gives some examples of a cardiac monitoring device embodying the invention but is not limiting; many variations are possible. The electrodes may be used to record biopotentials other than ECG, e.g. EMG or EEG. For example the device may have more than two electrodes. It could be provided with additional sensors, e.g. one or more accelerometers, contact sensors, temperature sensors etc.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A cardiac monitoring device configured to transmit to a remote receiver, the cardiac monitoring device comprising a wearable unit comprising:
   a substrate;
   at least two electrodes for measuring ECG signals;
   a data processing arrangement comprising a data processor; and
   a wireless transceiver;
   wherein the data processing arrangement is sealed within the substrate and arranged to receive the measured ECG signals from the at least two electrodes, to obtain sampled signal data by sampling each ECG signal associated with a heartbeat, and to process the sampled signal data in the data processor to extract first key data relating to that heartbeat; and
   wherein the data processor is programmed to apply a time window to the sampled signal data to isolate at least a portion of the data associated with a given heartbeat and to measure amplitude changes in that window, and to use the amplitude changes to identify the first key data, the first key data comprising a time stamp of an R-peak in a QRS complex in the ECG signal and at least one further time or amplitude value corresponding to one or more pre-defined features of the ECG signal;
   wherein the at least one further time or amplitude value corresponding to the one or more pre-defined features of the ECG signal is chosen from one or more of: (i) R-S amplitude; (ii) temporal position of a P-wave; (iii) amplitude of a P-wave; (iv) amplitude variations in a P-wave; (v) temporal position of a T-wave; (vi) amplitude of a T-wave; (vii) amplitude of an S-T segment; and (viii) temporal extent of a Q-T interval wherein the data processor is configured to cause the wireless transceiver i) to transmit the first key data, and ii) after the first key data has been transmitted, to receive an instruction to re-program the data processor;

wherein the data processor is configured to implement the instruction received by the wireless transceiver to re-program the data processor to use the amplitude changes to identify second key data which is different from the first key data, wherein re-programming the data processor comprises changing the one or more pre-defined features of the ECG signal to one or more different pre-defined features of the ECG signal that are of interest for a particular subject being monitored, the second key data thereby comprising:

the time stamp of the R-peak in the QRS complex in the ECG signal; and at least one different further time or amplitude value corresponding to the one or more different pre-defined features of the ECG signal that are of interest for the particular subject being monitored, wherein the at least one different further time or amplitude value of the second key data is different from the one or more further time or amplitude value of the first key data and is chosen from one or more of: (i) R-S amplitude; (ii) temporal position of a P-wave; (iii) amplitude of a P-wave; (iv) amplitude variations in a P-wave; (v) temporal position of a T-wave; (vi) amplitude of a T-wave; (vii) amplitude of an S-T segment; and (viii) temporal extent of a Q-T interval; and wherein the data processor is configured to cause the wireless transceiver to transmit the second key data instead of the first key data after the data processor has been re-programmed.

2. A cardiac monitoring device as claimed in claim 1, wherein the data processor digitises the measured ECG signals at a rate of around 1 kHz.

3. A cardiac monitoring device as claimed in claim 1, wherein the data processor is programmed or re-programmed to run an identification algorithm that identifies a particular pre-defined feature of interest in the ECG signal.

4. A cardiac monitoring device as claimed in claim 1, wherein the data processing arrangement comprises a memory and the data processor is programmed or re-programmed during use to run a particular algorithm selected from a number of programs stored in the memory.

5. A cardiac monitoring device as claimed in claim 1, wherein the data processor is arranged to simultaneously perform amplitude calibration based on the amplitudes measured in each window.

6. A cardiac monitoring device as claimed in claim 1, wherein an analysis of the first or second key data results in an instruction for the device to operate in another mode of operation in which the data processor is configured to cause the wireless transceiver to transmit the measured ECG signals.

7. A cardiac monitoring device as claimed in claim 1, wherein the wireless transceiver is arranged to transmit the first or second key data to the remote receiver on a real-time basis.

8. A cardiac monitoring device as claimed in claim 1, wherein the wireless transceiver is arranged to transmit a message for each heartbeat.

9. A cardiac monitoring device as claimed in claim 1, wherein the data processor is programmed or re-programmed during use by the wireless transceiver receiving a new algorithm downloaded from a remote controller or gateway device.

10. A cardiac monitoring device as claimed in claim 1, wherein the wireless transceiver is arranged to transmit the first or second key data to a handheld receiver comprising a display and a user interface.

* * * * *